(12) United States Patent
Mo et al.

(10) Patent No.: US 11,974,985 B2
(45) Date of Patent: May 7, 2024

(54) COMPOSITION OF AMINOPYRAN DERIVATIVE

(71) Applicant: HAISCO PHARMACEUTICAL GROUP CO., LTD., Shannan (CN)

(72) Inventors: Yi Mo, Chengdu (CN); Honghu Li, Chengdu (CN); Xing Wan, Chengdu (CN); Fei Ye, Chengdu (CN)

(73) Assignee: HAISCO PHARMACEUTICAL GROUP CO., LTD., Shannan (CN)

( * ) Notice: Subject to any disclaimer, the term of this patent is extended or adjusted under 35 U.S.C. 154(b) by 923 days.

(21) Appl. No.: 16/967,534

(22) PCT Filed: Jan. 30, 2019

(86) PCT No.: PCT/CN2019/073912
§ 371 (c)(1),
(2) Date: Aug. 5, 2020

(87) PCT Pub. No.: WO2019/154218
PCT Pub. Date: Aug. 15, 2019

(65) Prior Publication Data
US 2021/0059987 A1    Mar. 4, 2021

(30) Foreign Application Priority Data

Feb. 6, 2018  (CN) .......................... 201810108653.X

(51) Int. Cl.
| A61K 31/4162 | (2006.01) |
| A61K 9/20 | (2006.01) |
| A61K 9/28 | (2006.01) |
| A61K 31/4188 | (2006.01) |

(52) U.S. Cl.
CPC ........ *A61K 31/4162* (2013.01); *A61K 9/2018* (2013.01); *A61K 9/2054* (2013.01); *A61K 9/28* (2013.01); *A61K 31/4188* (2013.01)

(58) Field of Classification Search
CPC ............ A61K 31/4162; A61K 31/4188; A61K 9/2018; A61K 9/28
USPC ...................................................... 514/406
See application file for complete search history.

(56) References Cited

U.S. PATENT DOCUMENTS

| 8,143,289 B2 * | 3/2012 | Biftu | .................... | C07D 487/04 |
| | | | | 548/360.5 |
| 8,455,533 B2 * | 6/2013 | Biftu | .................... | C07D 487/04 |
| | | | | 548/360.5 |

| 2012/0149637 A1 | 6/2012 | Biftu et al. |
| 2012/0149734 A1 | 6/2012 | Biftu et al. |
| 2016/0166544 A1 | 6/2016 | Cooper et al. |

FOREIGN PATENT DOCUMENTS

| CN | 101410400 A | 4/2009 | |
| CN | 106540265 A | 3/2017 | |
| CN | 106632349 A | 5/2017 | |
| CN | 106928228 A | 7/2017 | |
| CN | 109796455 A | 5/2019 | |
| CN | 111253403 A | 6/2020 | |
| EP | 3181565 A1 * | 6/2017 | .......... A61K 31/381 |
| EP | 3335702 A1 | 6/2018 | |
| EP | 3335703 A1 | 6/2018 | |
| WO | 2009014676 A1 | 1/2009 | |
| WO | 2011028455 A1 | 3/2011 | |
| WO | 2015031228 A1 | 3/2015 | |
| WO | 2015192701 A1 | 12/2015 | |
| WO | 2015192714 A1 | 12/2015 | |
| WO | 2017032705 A1 | 3/2017 | |
| WO | WO-2017107791 A1 * | 6/2017 | ......... A61K 31/4162 |
| WO | 2017202357 A1 | 11/2017 | |
| WO | 2017202365 A1 | 11/2017 | |

OTHER PUBLICATIONS

Extended European Search Report dated Nov. 15, 2021 for counterpart European Patent Application No. 19750607.4.
Office Action dated Oct. 26, 2021 for counterpart Japanese Patent Application No. 2020-542601.
PCT International Search Report for International Application No. PCT/CN2019/073912, dated Apr. 26, 2019, 9 pages.
Examination Report dated Jan. 12, 2021 for counterpart Indian patent application No. 202027033926.
First Office Action dated Aug. 11, 2022 for counterpart Chinese patent application No. 201980012017.X, 24 pages.
Search Report dated Aug. 11, 2022 for counterpart Chinese patent application No. 201980012017.X, 7 pages.

* cited by examiner

*Primary Examiner* — Kahsay Habte
(74) *Attorney, Agent, or Firm* — Hoffman Warnick LLC

(57) ABSTRACT

The present invention relates to a composition of a compound of general formula (A), a pharmaceutically acceptable salt or a prodrug, and a preparation method therefor.

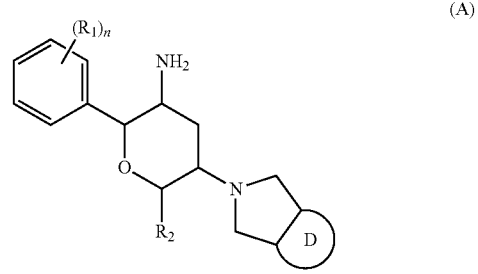

(A)

22 Claims, No Drawings

COMPOSITION OF AMINOPYRAN DERIVATIVE

TECHNICAL FIELD

The present invention relates to a composition of aminopyran derivatives, and more specifically, to an oral solid formulation containing aminopyran derivatives and a preparation method thereof.

BACKGROUND

International patent applications WO2015/192701 and WO2015/192714 disclose a series of aminopyran ring derivatives which are good DPPIV inhibitors and have the potential to prevent and/or treat type 2 diabetes, such as the compound of formula (I), the compound of formula (II), the compound of formula (III) (which is the dihydrochloride salt of compounds of formula (II)) and other related structures that have hypoglycemic functions and can be used to treat type 2 diabetes, with the structures shown as follows:

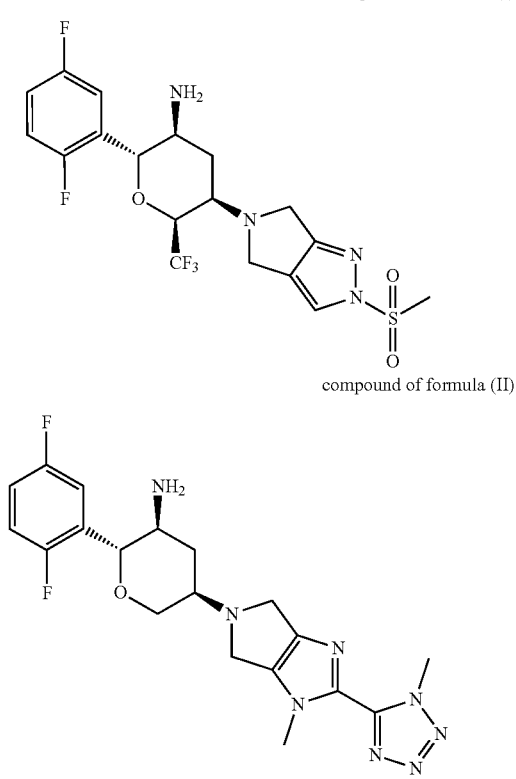

SUMMARY OF THE INVENTION

The compound of general formula (A), the compound of formula (I), the compound of formula (II) or the compound of formula (III) of the present invention have the disadvantages of easily generating impurities, instability, uncontrollable quality, and unfavorable preparation of pharmaceutical formulations.

The invention provides a formulation of aminopyran derivatives for the convenience of patients, which formulation is characterized in its stability, less impurities and controllable quality.

The present invention provides a formulation of the compound of general formula (A), the compound of formula (I), the compound of formula (II) or the compound of formula (III) containing neutral auxiliary materials, which overcomes the disadvantages of easily generating impurities, instability, uncontrollable quality and unfavorable preparation of pharmaceutical formulations.

The present invention provides a formulation of the compound of general formula (A), the compound of formula (I), the compound of formula (II) or the compound of formula (III) that does not contain reducing sugars, which overcomes the disadvantages of easily generating impurities, instability, uncontrollable quality and unfavorable preparation of pharmaceutical formulations.

The invention provides a preparation method of the formulation of the compound of general formula (A), the compound of formula (I), the compound of formula (II) or the compound of formula (III).

The present invention provides a compound of general formula (A) and its stereoisomer, or a pharmaceutically acceptable salt or prodrug thereof, wherein

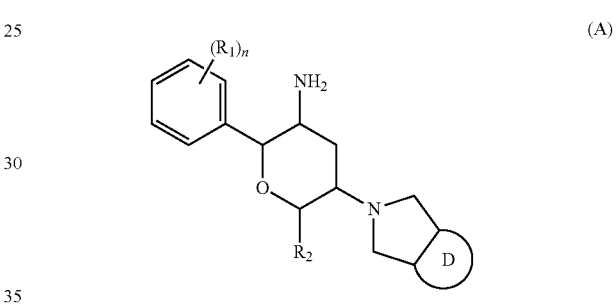

$R^1$ is each independently selected from H, F, Cl, Br or I;

$R^2$ is each independently selected from H, F, Cl, Br, I or $C_{1-4}$ alkyl, wherein the alkyl is optionally further substituted by 0, 1, 2, 3 or 4 substituents selected from H, F, Cl, Br or I; Ring D is selected from a 5-membered heteroaryl ring group, wherein the heteroaryl ring group is optionally further substituted by 0, 1, 2, 3 or 4 substituents selected from H, $C_{1-4}$ alkyl, $S(=O)_2$—$C_{1-4}$ alkyl or $D^1$, and the heteroaryl ring group contains 2 or 3 N atoms;

$D^1$ is each independently selected from a 5-membered heteroaryl ring group, wherein the heteroaryl ring group is optionally further substituted by 0, 1, 2, 3 or 4 substituents selected from H or $C_{1-4}$ alkyl, and the heteroaryl ring group contains 2, 3 or 4 N atoms;

n is selected from 0, 1, 2, 3, 4 or 5.

In a specific example, a compound of general formula (A) and its stereoisomers, or a pharmaceutically acceptable salt or prodrug thereof, wherein $R^1$ is each independently selected from H or F; $R^2$ is each independently selected from H or trifluoromethyl;

Ring D is selected from imidazole or pyrazole, wherein the imidazole or pyrazole is optionally further substituted by 0, 1, 2, 3 or 4 substituents selected from H, methyl, ethyl, isopropyl $S(=O)_2$-methyl, $S(=O)_2$-ethyl, $S(=O)_2$-isopropyl or $D^1$;

$D^1$ is each independently selected from tetrazole, wherein the tetrazole is optionally further substituted by 0, 1, 2, 3 or 4 substituents selected from H, methyl, ethyl or isopropyl;

n is selected from 0, 1, 2, 3, 4 or 5.

In a specific example, a compound of general formula (A) and its stereoisomer, or a pharmaceutically acceptable salt or prodrug thereof, wherein the pharmaceutically acceptable salt is selected from benzenesulfonate, salicylate, benzoate, acetate, S-(+)-mandelate, propionate, crotonate, furoate, cinnamate, ethanesulfonate, glycolate, lactate, fumarate, formate, sulfate, hydrobromide, phosphate, trifluoroacetate, tartrate, citrate, glycolate, hydrochloride, p-toluenesulfonate, maleate, succinate, oxalate, methanesulfonate, malonate or malate.

In a specific example, a compound of general formula (A) and its stereoisomer, or a pharmaceutically acceptable salt or prodrug thereof, wherein the compound of formula (A) is selected from one of the following structures:

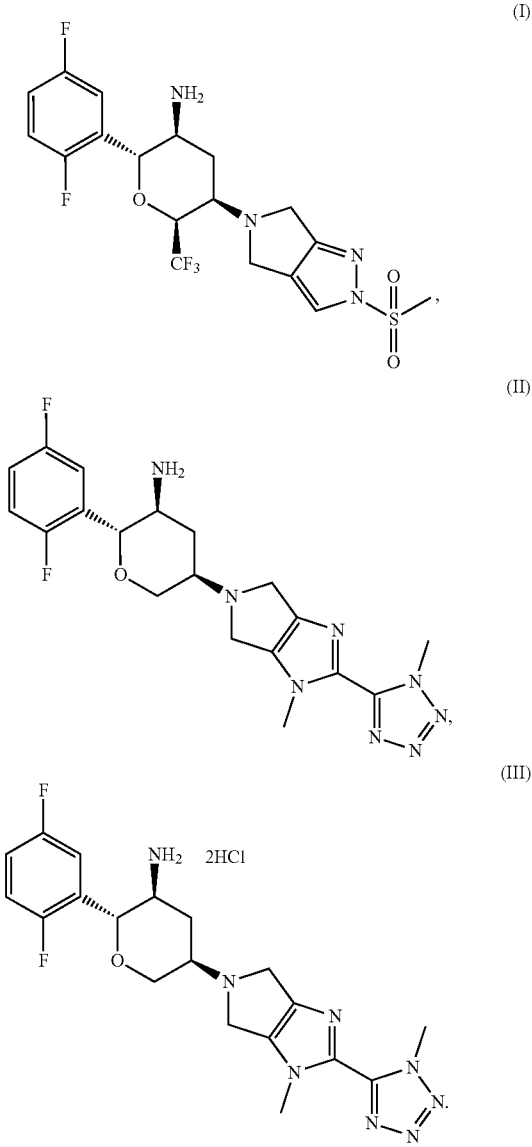

The present invention provides a stable pharmaceutical formulation containing the compound of general formula (A), the compound of formula (I), the compound of formula (II) or the compound of formula (III), comprising a formulation unit including but are not limited to a unit of 0.1-1 mg, 1-5 mg, 5-10 mg, 10-15 mg, 15-20 mg, 20-25 mg, 25-30 mg, 30-35 mg, 35-40 mg, 40-45 mg and 45-50 mg of the compound of general formula (A), the compound of formula (I), the compound of formula (II) or the compound of formula (III); more specifically, this formulation comprises a formulation unit including but not limited to a unit of 0.5 mg, 5 mg, 10 mg, 12.5 mg, 15 mg, 20 mg, 25 mg and 30 mg of the compound of general formula (A), the compound of formula (I), the compound of formula (II) or the compound of formula (III); more preferably, a unit of 5 mg, 12.5 mg, 15 mg, 25 mg, 30 mg of the compound of general formula (A), the compound of formula (I), the compound of formula (II) or the compound of formula (III).

The compound of general formula (A), the compound of formula (I), the compound of formula (II) or the compound of formula (III) is comprised in the formulation in a percentage including but not limited to 0.1%-50% by weight, 0.1%-1% by weight, 0.1%-2% by weight, 0.1%-5% by weight, 1%-10% by weight, 5%-10% by weight, 10%-25% by weight, 20%-35% by weight, 30-40% by weight, 25%-50% by weight. For example, the compound of general formula (A), the compound of formula (I), the compound of formula (II) or the compound of formula (III) is comprised in the formulation in a percentage selected from but not limited to 0.1% by weight, 0.7% by weight, 1% by weight, 7.1% by weight, 25.0% by weight, 8.3% by weight, 21.4% by weight, 31.5% by weight, 31.3% by weight, 37.5% by weight, 41.7% by weight, preferably for formulations with high drug loading.

In a specific example, the content of the compound of general formula (A), the compound of formula (I), the compound of formula (II) or the compound of formula (III) in the formulation is selected from 0.1%-50% by weight, 0.1%-1% by weight, 0.1%-2% by weight, 0.1%-5% by weight, 1%-10% by weight, 5%-10% by weight, 10%-25% by weight, 20%-35% by weight, 0.1%-0.2% by weight, 0.6%-0.8% by weight, 7.0%-9.0% by weight, 6.0%-8.0% by weight, 20.5%-22.5% by weight, 24.0%-26.0% by weight, 30.0%-32.0% by weight, 36.5%-38.5% by weight.

In the formulation of the compound of general formula (A), the compound of formula (I), the compound of formula (II) or the compound of formula (III), the auxiliary material used is preferably a neutral diluent that does not comprise reducing sugar or a mixture of reducing sugars (a trivial amount of reducing sugar is allowable in the form of impurities in the diluent). The types of auxiliary materials include but are not limited to diluents, disintegrants, lubricants, glidants, surfactants, antioxidants or sweeteners.

The neutral diluent is a diluent having no ionic charge.

In specific examples of the present invention, the auxiliary materials used is comprised in the formulation in a percentage of not less than 90% by weight. In other specific examples of the present invention, the auxiliary materials used is comprised in the formulation in a percentage of not less than 80% by weight. In yet some other specific examples of the present invention, the auxiliary materials used is comprised in the formulation is not less than 70% by weight. In still some other specific examples of the present invention, the percentage of the auxiliary materials used is comprised in the formulation in a percentage of not less than 60% by weight. In some other specific examples of the present invention, the auxiliary materials used is comprised in the formulation in a percentage of not less than 50% by weight. In yet some other specific examples of the present invention, the auxiliary materials used is comprised in the formulation in a percentage of not less than 40% by weight.

In specific examples of the present invention, auxiliary materials used is comprised in the formulation in a percentage selected from 90%-99.9%, 80%-99.9%, 70%-99.9%, 60%-99.9%, 50%-99.9%, 40%-99.9% by weight.

The diluent used in the present invention includes but are not limited to one or more of sucrose, mannitol, microcrystalline cellulose, xylitol, maltitol, lactitol, starch, pregelatinized starch, hydroxypropyl cellulose, hydroxypropyl methyl cellulose and sorbitol. The diluent preferably used in the present invention includes but is not limited to one or more of mannitol, microcrystalline cellulose, starch, or pregelatinized starch.

The diluent selected for the pharmaceutical formulation of the compound of general formula (A), the compound of formula (I), the compound of formula (II) or the compound of formula (III) in the present invention does not include lactose monohydrate, siliconized microcrystalline cellulose, hydroxyethyl cellulose, anhydrous lactose, glucose, maltose and other reducing sugars.

In specific examples of the present invention, the diluent is comprised in the formulation in a percentage of 80%-90% by weight. In some other specific examples of the present invention, the diluent is comprised in the formulation in a percentage of 70%-80% by weight.

In yet some other specific examples of the present invention, the diluent is comprised in the formulation in a percentage of 60%-70% by weight. In still some other specific examples of the present invention, the diluent is comprised in the formulation in a percentage of 50%-60% by weight.

In a specific example, the diluent is comprised in the formulation in a percentage selected from 40%-96%, 50%-96%, 60%-96%, 70%-96%, 80%-96% or 90%-96%, 50%-99% by weight.

In specific examples of the present invention, the amount of the diluent used in the unit formulation includes but is not limited to 10-50 mg, 20-50 mg, 30-50 mg, 40-50 mg. In some other specific examples, the amount of diluent used in the unit formulation includes but is not limited to 20-60 mg, 30-60 mg, 40-60 mg, 50-60 mg. In yet some other specific examples, the amount of the diluent used in the unit formulation includes but is not limited to 20-70 mg, 30-70 mg, 40-70 mg, 50-70 mg, 60-70 mg. In still some other specific examples, the amount of the diluent used in the unit formulation includes but is not limited to 30-80 mg, 40-80 mg, 50-80 mg, 60-80 mg, 70-80 mg. In some other specific examples, the amount of the diluent used in the unit formulation includes but is not limited to 40-90 mg, 50-90 mg, 60-90 mg, 70-90 mg, 80-90 mg. In yet some other specific examples, the amount of the diluent used in the unit formulation includes but is not limited to 40-100 mg, 50-100 mg, 60-100 mg, 70-100 mg, 80-100 mg.

In some other specific examples, the amount of the diluent used in the unit formulation includes but is not limited to 100-150 mg, 110-150 mg, 120-150 mg, 130-150 mg, 140-150 mg. In yet some other specific examples, the amount of the diluent in the unit formulation includes but is not limited to 150-200 mg, 160-200 mg, 170-200 mg, 180-200 mg, 190-200 mg. In still some other specific examples, the amount of the diluent used in the unit formulation includes but is not limited to 200-250 mg, 210-250 mg, 220-250 mg, 230-250 mg, 240-250 mg. In some other specific examples, the amount of the diluent used in the unit formulation includes but is not limited to 250-300 mg, 260-300 mg, 270-300 mg, 280-300 mg, 290-300 mg. In yet some other specific examples, the amount of the diluent used in the unit formulation includes but is not limited to 300-350 mg, 310-350 mg, 320-350 mg, 330-350 mg, 340-350 mg.

In specific examples of the present invention, the diluent selected is a mixture of two diluents, preferably microcrystalline cellulose and mannitol in the present invention. In a specific example, the mixture is comprised in the formulation in a percentage of 40%-96% by weight, and the microcrystalline cellulose is comprised in the mixture is 55%-75% by weight. The mixture is comprised in the formulation in a percentage of 40%-90% by weight, wherein the microcrystalline cellulose is comprised in the mixture in a percentage of 40%-60% by weight. In another specific example, the mixture is comprised in the formulation in a percentage of 50%-90% by weight, wherein microcrystalline cellulose is comprised in the mixture in a percentage of 50%-70% by weight. In another specific example, the mixture is comprised in the formulation in a percentage of 60%-90% by weight, wherein the microcrystalline cellulose is comprised in the mixture in a percentage of 10%-50% by weight. In another specific example, the mixture is comprised in the formulation in a percentage of 70%-90% by weight, wherein microcrystalline cellulose is comprised in the mixture in a percentage of 20%-50% by weight.

In a specific example, the diluent is selected as a mixture of two diluents, preferably microcrystalline cellulose and mannitol in the present invention. The content of the mixture in the formulation is selected from a percentage of 40%-96% by weight, 50%-90% by weight, 60%-90% by weight, 70%-96% by weight, 80%-96% by weight, 90%-96% by weight, wherein the content of the microcrystalline cellulose in the mixture is selected from a percentage of 10%-90% by weight, 40%-60% by weight, 10%-50% by weight, 50%-70% by weight, 55%-75% by weight, 20%-50% by weight.

In a specific example, the diluent selected is a mixture of two diluents, preferably microcrystalline cellulose and mannitol in the present invention. In a specific example, the amount of the mixture used in the unit formulation is 30-50 mg, wherein the amount of microcrystalline cellulose is 30-40 mg. In another specific example, the amount of the mixture in the unit formulation is 30-60 mg, wherein the amount of microcrystalline cellulose is 20-40 mg. In another specific example, the amount of the mixture in the unit formulation is 30-70 mg, wherein the amount of microcrystalline cellulose is 10-40 mg.

In another specific example, the amount of the mixture in the unit formulation is 30-80 mg, wherein the amount of microcrystalline cellulose is 10-50 mg. In another specific example, the amount of the mixture in the unit formulation is 80-100 mg, wherein the amount of microcrystalline cellulose is 20-50 mg. In another specific example, the amount of the mixture in the unit formulation is 80-120 mg, wherein the amount of microcrystalline cellulose is 20-60 mg. In another specific example, the amount of the mixture in the unit formulation is 80-140 mg, wherein the amount of microcrystalline cellulose is 20-70 mg. In another specific example, the amount of the mixture in the unit formulation is 100-160 mg, wherein the amount of microcrystalline cellulose is 30-80 mg. In another specific example, the amount of the mixture in the unit formulation is 100-180 mg, wherein the amount of microcrystalline cellulose is 30-90 mg. In another specific example, the amount of the mixture in the unit formulation is 100-200 mg, wherein the amount of microcrystalline cellulose is 30-100 mg. In another specific example, the amount of the mixture in the unit formulation is 100-220 mg, wherein the amount of microcrystalline cellulose is 30-110 mg. In another specific example, the amount of the mixture in the unit formulation is 100-240 mg, wherein the amount of microcrystalline cellulose is 30-120 mg. In another specific example, the amount of the mixture in the unit formulation is 100-260 mg, wherein the amount of microcrystalline cellulose is 30-130 mg.

In a specific example, the formulation contains 34.81 mg of microcrystalline cellulose and 17.40 mg of mannitol.

In a specific example, the formulation contains 15.00 mg of microcrystalline cellulose and 37.22 mg of mannitol.

In a specific example, the formulation contains 17.4 mg of microcrystalline cellulose and 34.8 mg of mannitol.

In a specific example, the formulation contains 55.59 mg of microcrystalline cellulose and 111.18 mg of mannitol.

In specific examples of the present invention, the pharmaceutical formulation contains one or more lubricants or glidants. The lubricants include but are not limited to one or more of magnesium stearate, calcium stearate, stearic acid, sodium stearyl fumarate, hydrogenated castor oil. In the present invention, magnesium stearate is preferred. The glidants include but are not limited to one or more of colloid silica, calcium phosphate, magnesium silicate, and talc.

In a specific example, the amount of lubricant used in the unit formulation includes but is not limited to 0.25-0.5 mg, 0.25-0.6 mg, 0.25-0.7 mg, 0.25-0.8 mg, 0.25-0.9 mg, 0.25-1.0 mg, 0.25-1.1 mg, 0.25-1.2 mg, 0.25-1.3 mg, 0.25-1.4 mg, 0.25-1.5 mg, 1.0-2.0 mg, 1.0-2.5 mg, 1.0-3.0 mg, 1.0-3.5 mg, 1.0-4.0 mg, 1.0-4.5 mg, 1.0-5.0 mg.

In a specific example, the amount of glidant used in the unit formulation includes but is not limited to 1-5 mg, 2-6 mg, 3-7 mg, 4-8 mg.

In a specific example, the amount of lubricant used in the formulation includes but is not limited to a percentage of 0.05%-0.1%, 0.05%-0.5%, 0.05%-1%, 0.05%-2%, 0.05%-3%, 1%-2%, 1%-3%, 2%-3%, 2%-4%, 2%-5% by weight. In a specific example, the amount of glidant used in the formulation includes but is not limited to a percentage of 1%-2%, 1%-3%, 1%-4%, 1%-5% by weight.

Appropriate amount of the lubricant used allows the pharmaceutical formulation to have better appearance and shape, suitable hardness, and moderate disintegration time. Therefore, the amount of the lubricant used is essential for the pharmaceutical formulation of the compound of general formula (A), the compound of formula (I), the compound of formula (II) or the compound of formula (III). In the present application, a lubricant of 2% or more by weight per unit dose can provide the compound of general formula (A), the compound of formula (I), the compound of formula (II) or the compound of formula (III) with good hardness, disintegration and tablet appearance.

In a specific example, the pharmaceutical formulation may include disintegrants, including but not limited to one or more of croscarmellose sodium, sodium carboxymethyl starch, low-substituted hydroxypropyl cellulose, crospovidone, and calcium carboxymethyl cellulose. In a specific embodiment, the disintegrant is crospovidone.

In a specific example, the amount of disintegrant used in the formulation includes but is not limited to a percentage of 1%-2%, 1%-3%, 1%-4%, 1%-5%, 1%-6% by weight.

In a specific example, the pharmaceutical formulation may contain one or more neutral surfactants or wetting agents. The neutral surfactant includes but are not limited to one or more of glyceryl monooleate, polysorbate, polyvinyl alcohol, and sorbate. The wetting agent includes but are not limited to one or more of poloxamers, polyoxyethylene alkyl ethers, polyoxyethylene castor oil derivatives, and polyoxyethylene stearate.

In a specific example, the pharmaceutical formulation may further include antioxidants to increase the stability of the formulation, including but not limited to one or more of vitamin E, alpha-tocopherol, vitamin C and its related sodium or calcium salts, vitamin C palmitate, propyl gallate, octyl gallate, lauryl gallate, butylated hydroxytoluene (BHT), butylated hydroxyanisole (BHA). In a specific example, the antioxidant is selected from one or more of BHT or BHA.

In a specific example, the percentage of the amount of the antioxidant used in the formulation includes but is not limited to a percentage of 0%-2%, 0%-1%, 0.1%-1%, 0.2%-0.8%, 0.4%-0.8% by weight.

In a specific example, the auxiliary materials described in the pharmaceutical formulation may further include one or more of lubricants, glidants, disintegrants, surfactants, wetting agents, and antioxidants.

In a specific example, the lubricant described in the pharmaceutical formulation is selected from one or more of magnesium stearate, calcium stearate, stearic acid, sodium stearyl fumarate, and hydrogenated castor oil; the glidant is selected from one or more of colloid silica, calcium phosphate, magnesium silicate and talc; the disintegrant is selected from one or more of croscarmellose sodium, sodium carboxymethyl starch, crospovidone and calcium carboxymethyl cellulose; the surfactant is selected from one or more of glycerol monooleate, polysorbate, polyvinyl alcohol, and sorbate; the wetting agent is selected from one or more of poloxamer, polyoxyethylene alkyl ether, polyoxyethylene castor oil derivatives, and polyoxyethylene stearate; the antioxidant is selected from one or more of vitamin E, alpha-tocopherol, vitamin C and their related sodium salts or calcium salts, vitamin C palmitate, propyl gallate, octyl gallate, lauryl gallate, butylated hydroxytoluene (BHT), and butylated hydroxyanisole (BHA).

In a specific example, the content of lubricant in the pharmaceutical formulation is selected from 0.05%41% by weight, 0.05%-0.5% by weight, 0.05%-1% by weight, 0.05%-2% by weight, 0.05%-3% by weight, 1%-2% by weight, 1%-3% by weight, 2%-3%, 2%-4% by weight; the content of glidant is selected from 1%-2% by weight, 1%-3% by weight, 1%-4% by weight, 1%-5% by weight; the content of disintegrant is selected from 1%-5% by weight, 1%-3% by weight; the content of antioxidant is selected from 0%-2%, 0%-1%, 0.1%-1% by weight, 0.2%-0.8% by weight, 0.4%-0.8% by weight.

The compound of general formula (A), the compound of formula (I), the compound of formula (II) or the compound of formula (III) is preferably in the dosage form of tablet, including but not limited to tableting by wet granulation or dry granulation and direct tableting; in a specific example, it is an uncoated tablet; in another example, it is a tablet coated with Kalekon immediate-release coating powder which contains hydroxypropyl methylcellulose; in a specific example, it is a Uteki EPO coating powder-coated tablet.

In a specific example, the formulation may further optionally include or not include flavoring agent or sweetener.

In a specific example, the pharmaceutical formulation contains 1%-38% (W/W) of the compound of general formula (A), the compound of formula (I), the compound of formula (II) or the compound of formula (III), 0.4%-0.8% (W/W) of BHT, 50%-96% (W/W) of a mixture of microcrystalline cellulose and mannitol or 50%-96% (W/W) of a mixture of microcrystalline cellulose and pregelatinized starch, 2% of crospovidone, 2% of magnesium stearate.

In a specific example, the pharmaceutical formulation contains 1%-38% by weight of the compound of general formula (A), the compound of formula (I), the compound of formula (II) or the compound of formula (III), 0%-0.8% by weight of antioxidant, 50%-96% by weight of diluent, 1%-3% by weight of disintegrant, 1%-3% by weight of lubricant.

In a specific example, the pharmaceutical formulation contains 1%-38% by weight of the compound of general formula (A), the compound of formula (I), the compound of formula (II) or the compound of formula (III), 0%-0.8% by weight of BHT, 50%-96% by weight of a mixture of microcrystalline cellulose and mannitol or 50%-96% by weight of a mixture of microcrystalline cellulose and pregelatinized starch, 1%-3% by weight of crospovidone, 1%-3% by weight of magnesium stearate.

In a specific example, the content of the compound of general formula (A), the compound of formula (I), the compound of formula (II) or the compound of formula (III) contained in the pharmaceutical formulation is selected from 0.1%-50% by weight, 0.1%4% by weight, 0.1%-2% by weight, 0.1%-5% by weight, 1%-10% by weight, 5%-10% by weight, 10%-25% by weight, 20%-35% by weight, 0.1%-0.2% by weight, 0.6%-0.8% by weight, 7.0%-9.0% by weight, 6.0%-8.0% by weight, 20.5%-22.5% by weight, 24.0%-26.0% by weight, 30.0%-32.0% by weight, 36.5%-38.5% by weight.

In a specific example, the formulation of the compound of formula (I) contains 0.5 mg of the compound of formula (I), 0.38 mg of antioxidant, 47.12 mg of a non-reducing sugar diluent or non-reducing sugar diluent mixture, 1.0 mg of disintegrant, 1.0 mg of lubricant.

In a specific example, the formulation of the compound of formula (I) contains 0.5 mg of the compound of formula (I), 0.38 mg of BHT, 30.4 mg of microcrystalline cellulose, 16.72 mg of mannitol, 1.0 mg of crospovidone, 1.0 mg of magnesium stearate.

In a specific example, the formulation of the compound of formula (I) contains 5 mg of the compound of formula (I), 0.38 mg of antioxidant, 52.22 mg of non-reducing sugar diluent or non-reducing sugar diluent mixture, 1.2 mg of disintegrant, 1.2 mg of lubricant.

In a specific example, the formulation of the compound of formula (I) contains 5 mg of the compound of formula (I), 0.38 mg of BHT, 36.46 mg of microcrystalline cellulose, 15.76 mg of mannitol, 1.2 mg of crospovidone, 1.2 mg of magnesium stearate.

In a specific example, the formulation of the compound of formula (I) contains 25 mg of the compound of formula (I), 0.38 mg of antioxidant, 51.42 mg of non-reducing sugar diluent or non-reducing sugar diluent mixture, 1.6 mg of disintegrant, 1.6 mg of lubricant.

In a specific example, the formulation of the compound of formula (I) contains 25 mg of the compound of formula (I), 0.38 mg of BHT, 36.42 mg of microcrystalline cellulose, 15 mg of mannitol, 1.6 mg of crospovidone, 1.6 mg of magnesium stearate.

The formulation described here can be made into tablets by wet granulation or dry granulation or direct tableting. In a specific example, the formulation is made into granules by a wet granulator followed by tableting. In another specific example, a fluidized bed is used to prepare the granules, which are then tableted.

In other specific examples, the formulations described are prepared by direct tableting or dry granulation followed by tableting. Dry granulation tableting uses a dry granulator to obtain granules.

In a specific example, the formulation of the compound of formula (I) contains 0.5 mg of the compound of formula (I), 0.38 mg of antioxidant, 67.02 mg of non-reducing sugar diluent or non-reducing sugar diluent mixture, 1.4 mg of disintegrant, 0.7 mg of lubricant.

In a specific example, the formulation of the compound of formula (I) contains 0.5 mg of the compound of formula (I), 0.38 mg of BHT, 40 mg of microcrystalline cellulose, 27.02 mg of pregelatinized starch, 1.4 mg of crospovidone, 0.7 mg of magnesium stearate.

In a specific example, the formulation of the compound of formula (I) contains 5 mg of the compound of formula (I), 0.38 mg of antioxidant, 62.52 mg of non-reducing sugar diluent or non-reducing sugar diluent mixture, 1.4 mg of disintegrant, 0.7 mg of lubricant.

In a specific example, the formulation of the compound of formula (I) contains 5 mg of the compound of formula (I), 0.38 mg of BHT, 40 mg of microcrystalline cellulose, 22.52 mg of pregelatinized starch, 1.4 mg of crospovidone, 0.7 mg of magnesium stearate.

In a specific example, the formulation of the compound of formula (I) contains 25 mg of the compound of formula (I), 0.38 mg of antioxidant, 71.62 mg of non-reducing sugar diluent or non-reducing sugar diluent mixture, 2 mg of disintegrant, lmg of lubricant.

In a specific example, the formulation of the compound of formula (I) contains 25 mg of the compound of formula (I), 0.38 mg of BHT, 45 mg of microcrystalline cellulose, 26.62 mg of pregelatinized starch, 2 mg of crospovidone, 1 mg of magnesium stearate.

The formulation described here can be made into tablets by wet granulation or dry granulation or direct tableting. In a specific example, the formulation is made into granules by a wet granulator followed by tableting. In another specific example, a fluidized bed is used to prepare the granules, which are then tableted.

In other specific examples, the formulations described are prepared by direct tableting or dry granulation followed by tableting. Dry granulation tableting uses a dry granulator to obtain granules.

In a specific example, the formulation of the compound of formula (I) contains 0.5 mg of the compound of formula (I), 47.5 mg of non-reducing sugar diluent or non-reducing sugar diluent mixture, 1.0 mg of disintegrant, 1.0 mg of lubricant.

In a specific example, the formulation of the compound of formula (I) contains 0.5 mg of the compound of formula (I), 30.4 mg of microcrystalline cellulose, 17.1 mg of mannitol, 1.0 mg of crospovidone, 1.0 mg of magnesium stearate.

In a specific example, the formulation of the compound of formula (I) contains 5 mg of the compound of formula (I), 52.6 mg of non-reducing sugar diluent or non-reducing sugar diluent mixture, 1.2 mg of disintegrant, 1.2 mg of lubricant.

In a specific example, the formulation of the compound of formula (I) contains 5 mg of the compound of formula (I), 36.46 mg of microcrystalline cellulose, 16.14 mg of mannitol, 1.2 mg of crospovidone, 1.2 mg of magnesium stearate.

In a specific example, the formulation of the compound of formula (I) contains 25 mg of the compound of formula (I), 51.8 mg of non-reducing sugar diluent or non-reducing sugar diluent mixture, 1.6 mg of disintegrant, 1.6 mg of lubricant.

In a specific example, the formulation of the compound of formula (I) contains 25 mg of the compound of formula (I), 36.8 mg of microcrystalline cellulose, 15 mg of mannitol, 1.6 mg of crospovidone, 1.6 mg of magnesium stearate.

The formulation described here can be made into tablets by wet granulation or dry granulation or direct tableting. In a specific example, the formulation is made into granules by a wet granulator followed by tableting. In another specific example, a fluidized bed is used to prepare the granules, which are then tableted.

In other specific examples, the formulations described are prepared by direct tableting or dry granulation followed by tableting. Dry granulation tableting uses a dry granulator to obtain granules.

In a specific example, the formulation of the compound of formula (I) contains 0.5 mg of the compound of formula (I), 67.4 mg of non-reducing sugar diluent or non-reducing sugar diluent mixture, 1.4 mg of disintegrant, 0.7 mg of lubricant.

In a specific example, the formulation of the compound of formula (I) contains 0.5 mg of the compound of formula (I), 40 mg of microcrystalline cellulose, 27.4 mg of pregelatinized starch, 1.4 mg of crospovidone, 0.7 mg of magnesium stearate.

In a specific example, the formulation of the compound of formula (I) contains 5 mg of the compound of formula (I), 62.9 mg of non-reducing sugar diluent or non-reducing sugar diluent mixture, 1.4 mg of disintegrant, 0.7 mg of lubricant.

In a specific example, the formulation of the compound of formula (I) contains 5 mg of the compound of formula (I), 0.38 mg of BHT, 40 mg of microcrystalline cellulose, 22.9 mg of pregelatinized starch, 1.4 mg of crospovidone, 0.7 mg of magnesium stearate.

In a specific example, the formulation of the compound of formula (I) contains 25 mg of the compound of formula (I), 72 mg of non-reducing sugar diluent or non-reducing sugar diluent mixture, 2 mg of disintegrant, 1 mg of lubricant.

In a specific example, the formulation of the compound of formula (I) contains 25 mg of the compound of formula (I), 45 mg of microcrystalline cellulose, 27 mg of pregelatinized starch, 2 mg of crospovidone, 1 mg of magnesium stearate.

The formulation described here can be made into tablets by wet granulation or dry granulation or direct tableting. In a specific example, the formulation is made into granules by a wet granulator followed by tableting. In another specific example, a fluidized bed is used to prepare the granules, which are then tableted.

In other specific examples, the formulations described are prepared by direct tableting or dry granulation followed by tableting. Dry granulation tableting uses a dry granulator to obtain granules.

In a specific example, the formulation of the compound of formula (I) contains 0.5 mg of the compound of formula (I), 56.72 mg of non-reducing sugar diluent or non-reducing sugar diluent mixture, 1.2 mg of disintegrant, 1.2 mg of lubricant.

In a specific example, the formulation of the compound of formula (I) contains 0.5 mg of the compound of formula (I), 0.38 mg of BHT, 18.91 mg of microcrystalline cellulose, 37.81 mg of mannitol, 1.2 mg of crospovidone, 1.2 mg of magnesium stearate.

In a specific example, the formulation of the compound of formula (I) contains 5 mg of the compound of formula (I), 52.2 mg of non-reducing sugar diluent or non-reducing sugar diluent mixture, 1.2 mg of disintegrant, 1.2 mg of lubricant.

In a specific example, the formulation of the compound of formula (I) contains 5 mg of the compound of formula (I), 0.38 mg of BHT, 17.4 mg of microcrystalline cellulose, 34.8 mg of mannitol, 1.2 mg of crospovidone, 1.2 mg of magnesium stearate.

In a specific example, the formulation of the compound of formula (I) contains 25 mg of the compound of formula (I), 166.8 mg of non-reducing sugar diluent or non-reducing sugar diluent mixture, 4 mg of disintegrant, 4 mg of lubricant.

In a specific example, the formulation of the compound of formula (I) contains 25 mg of the compound of formula (I), 0.223 mg of BHT, 55.6 mg of microcrystalline cellulose, 111.2 mg of mannitol, 4 mg of crospovidone, 4 mg of magnesium stearate.

The formulation described here can be made into tablets by wet granulation or dry granulation or direct tableting. In a specific example, the formulation is made into granules by a wet granulator followed by tableting. In another specific example, a fluidized bed is used to prepare the granules, which are then tableted.

In other specific examples, the formulations described are prepared by direct tableting or dry granulation followed by tableting. Dry granulation tableting uses a dry granulator to obtain granules.

The present invention also provides a use of a pharmaceutical formulation for preparing a medicament for diabetes, wherein the pharmaceutical formulation contains a unit of 0.10 mg-50 mg of the compound of general formula (A), the compound of formula (I), the compound of formula (II) or the compound of formula (III); preferably, the pharmaceutical formulation contains a unit of 0.1-1 mg, 1-5 mg, 5-10 mg, 10-15 mg, 15-20 mg, 20-25 mg, 25-30 mg, 30-35 mg, 35-40 mg, 40-45 mg or 45-50 mg of the compound of general formula (A), the compound of formula (I), the compound of formula (II) or the compound of formula (III); more preferably, the pharmaceutical formulation contains a unit of 0.5 mg, 5 mg, 10 mg, 12.5 mg, 15 mg, 20 mg, 25 mg or 30 mg of the compound of general formula (A), the compound of formula (I), the compound of formula (II) or the compound of formula (III).

The present invention provides a use of a pharmaceutical formulation in the preparation of a medicament for diabetes, comprising administration of the pharmaceutical formulation described above to a subject.

The present invention provides a use of a pharmaceutical formulation in the preparation of a medicament for diabetes which is orally administered.

The present invention provides a use of a pharmaceutical formulation in the preparation of a medicament for diabetes. The administration includes oral administration once a day, once a week, once every two weeks, or once a month.

The present invention provides a use of a pharmaceutical formulation in the preparation of a medicament for diabetes, comprising administration of the pharmaceutical formulation described above to a subject. The compound of general formula (A), the compound of formula (I), the compound of formula (II) or the compound of formula (III) is administered in a dosage selected from 1-500 mg/dose.

The present invention provides a use of a pharmaceutical formulation in the preparation of a medicament for diabetes, comprising administration of the pharmaceutical formulation described above to a subject. The compound of general formula (A), the compound of formula (I), the compound of formula (II) or the compound of formula (III) is administered in a dosage selected from 1-400 mg/dose, 1-350 mg/dose, 1-300 mg/dose.

The present invention provides a use of a pharmaceutical formulation in the preparation of a medicament for diabetes, comprising administration of the pharmaceutical formulation described above to a subject. The compound of general formula (A), the compound of formula (I), the compound of formula (II) or the compound of formula (III) is administered in a dosage selected from 1-5 mg/dose, 5-10 mg/dose, 10-20 mg/dose, 20-25 mg/dose, 25-50 mg/dose, 50-75 mg/dose, 75-100 mg/dose, 100-125 mg/dose, 125-150 mg/dose, 150-175 mg/dose, 175-200 mg/dose, 200-225 mg/dose, 225-250 mg/dose, 250-275 mg/dose, 275-300 mg/dose.

The present invention provides a use of a pharmaceutical formulation in the preparation of a medicament for diabetes, comprising administration of the pharmaceutical formulation described above to a subject. The compound of general formula (A), the compound of formula (I), the compound of formula (II) or the compound of formula (III) is administered in a dosage selected from 5 mg/dose, 10 mg/dose, 20 mg/dose, 25 mg/dose, 50 mg/dose, 75 mg/dose, 100 mg/dose, 125 mg/dose, 150 mg/dose, 175 mg/dose, 200 mg/dose, 225 mg/dose, 250 mg/dose, 275 mg/dose, 300 mg/dose.

Unless stated to the contrary, the terms used in the specification and claims have the following meanings.

"Pharmaceutically acceptable salt" means safe, non-toxic and neither biologically nor otherwise undesirable, and includes pharmaceutically acceptable salts for veterinary use as well as human medical use with the desired pharmacological activity.

"Prodrug" refers to a compound of the present invention that can be metabolized in vivo to have biological activity. The prodrug of the present invention is prepared by modifying the phenol group in the compounds of the present invention. This modification can be removed by conventional operations or in vivo to obtain the parent compound. When the prodrug of the present invention is administered to a mammalian individual, the prodrug is cleaved to form free hydroxyl groups.

"Stereoisomer" refers to isomers formed with different special arrangement of atoms in a molecule, including cis-trans isomers, enantiomers and conformational isomers.

"Optional" or "optionally" or "selective" or "selectively" means that the subsequently described event or condition may but does not necessarily occur, and this expression encompasses the circumstances in which the event or condition occurs and those in which it does not occur. For example, "heterocyclic group optionally substituted with an alkyl group" means that the alkyl group may be but not necessarily present. The expression encompasses the case where the heterocyclic group is substituted with an alkyl group, and the case in which the heterocyclic group is not substituted with an alkyl group.

DETAILED DESCRIPTION OF THE INVENTION

The following Examples illustrate the technical solutions of the present invention in details, but the protection scope of the present invention includes these Examples but is not limited thereto.

The known starting materials in the present invention can be synthesized by or in accordance with methods known in the art, or can be purchased from Titan Technology Co., Ltd, Energy Chemical Co., Ltd, Shanghai DEMO Medical Tech Co., Ltd, ChengDu Chron Chemicals Co., Ltd, Accela ChemBio Co., Ltd., J&K Scientific Ltd, etc.

The compound of general formula (A) or its specific structures, the compound of formula (I), the compound of formula (II), and the compound of formula (III), can be prepared by the methods in patents WO2015/192701 and WO2015/192714.

Butylated hydroxytoluene, name: dibutyl hydroxy toluene, BHT, also known as dibutyl hydroxy toluene (Butylated Hydoxy Toluene), alias: 2,6-di-tert-butyl p-cresol, 3,5-di-tert-butyl-4-hydroxytoluene, BHT.

Butyl hydroxyanisole, name: butyl hydroxyanisole, BHA, also known as butyl hydroxyanisole, tert-butyl-4-hydroxyanisole, butyl anisole, BHA.

Examples 1-5

TABLE 1

| Raw materials and auxiliaries | Example 1 0.5 mg unit (%) | Example 2 5 mg unit (%) | Example 3 15 mg unit (%) | Example 4 25 mg unit (%) | Example 5 30 mg unit (%) |
|---|---|---|---|---|---|
| Compound of formula (I) | 1.00 | 8.33 | 21.43 | 31.25 | 37.50 |
| Butylated hydroxytoluene | 0.76 | 0.63 | 0.54 | 0.48 | 0.48 |
| Microcrystalline cellulose | 60.80 | 60.77 | 52.60 | 45.53 | 39.28 |
| Mannitol | 33.44 | 26.27 | 21.43 | 18.75 | 18.75 |
| Crospovidone | 2.00 | 2.00 | 2.00 | 2.00 | 2.00 |
| Magnesium stearate | 2.00 | 2.00 | 2.00 | 2.00 | 2.00 |
| Produced | 50 mg | 60 mg | 70 mg | 80 mg | 80 mg |

Preparation Method:

The raw materials and butylated toluene were weighted and mixed. In the above formulations, the active pharmaceutical ingredient (API) and butylated toluene were directly mixed for a 0.5 mg unit tablet, with proportional increment in principle for the 5 mg, 15 mg, 25 mg, and 30 mg unit prescriptions, until the API and butylated toluene were uniformly mixed.

Microcrystalline cellulose, mannitol and crospovidone were weighted and added to the mixture of the API and butylated toluene which was already uniformly mixed, and mixed evenly.

Magnesium stearate were weighted and added to the above mixture to complete the final blending.

The final blended powder was tableted to give the product.

Examples 6-8

TABLE 2

| Raw materials and auxiliaries | Example 6 0.5 mg unit (%) | Example 7 5 mg unit (%) | Example 8 25 mg unit (%) |
|---|---|---|---|
| Compound of formula (I) | 0.71 | 7.14 | 25.00 |
| Butylated hydroxytoluene | 0.54 | 0.54 | 0.38 |
| Microcrystalline cellulose | 57.14 | 57.14 | 45.00 |
| Pregelatinized starch | 38.60 | 32.17 | 26.62 |
| Crospovidone | 2.00 | 2.00 | 2.00 |
| Magnesium stearate | 1.00 | 1.00 | 1.00 |
| Produced | 70 mg | 70 mg | 100 mg |

For the formulations described herein, direct tableting was carried out in Examples 6 and 7 to obtain tablets.

For Example 8, a wet granulation machine was used to produce granules which were then tableted.

Examples 9-11

TABLE 3

| Raw materials and auxiliaries | Example 9 0.5 mg unit (%) | Example 10 5 mg unit (%) | Example 11 25 mg unit (%) |
|---|---|---|---|
| Compound of formula (I) | 1.00 | 8.33 | 31.25 |
| Microcrystalline cellulose | 60.80 | 60.77 | 46.00 |
| Mannitol | 34.20 | 26.90 | 18.75 |
| Crospovidone | 2.00 | 2.00 | 2.00 |
| Magnesium stearate | 2.00 | 2.00 | 2.00 |
| Produced | 50 mg | 60 mg | 80 mg |

For the formulations described herein, direct tableting was carried out in Examples 9 and 10 to obtain tablets. For Example 11, a wet granulator was used to produce granules which were then tableted.

Examples 12-14

TABLE 4

| Raw materials and auxiliaries | Example 12 0.5 mg unit (%) | Example 13 5 mg unit (%) | Example 14 25 mg unit (%) |
|---|---|---|---|
| Compound of formula (I) | 0.71 | 7.14 | 25.00 |
| Microcrystalline cellulose | 57.14 | 57.14 | 45.00 |
| Pregelatinized starch | 39.14 | 32.71 | 27.00 |
| Crospovidone | 2.00 | 2.00 | 2.00 |
| Magnesium stearate | 1.00 | 1.00 | 1.00 |
| Produced | 70 mg | 70 mg | 100 mg |

For the formulations described herein, direct tableting was carried out in Examples 12 and 13 to obtain tablets. For Example 14, a dry granulator was used to produce granules which were then tableted.

Examples 15-19

TABLE 5

| Raw materials and auxiliaries | Example 15 5 mg unit (%) | Example 16 5 mg unit (%) | Example 17 5 mg unit (%) | Example 18 5 mg unit (%) | Example 19 5 mg unit (%) |
|---|---|---|---|---|---|
| Compound of formula (I) | 0.83 | 0.83 | 0.83 | 0.83 | 0.83 |
| Butylated hydroxytoluene | 0.63 | 0.63 | 0.63 | 0.63 | 0.63 |
| Microcrystalline cellulose | 65.28 | 58.02 | 43.52 | 29.01 | 21.76 |
| Mannitol | 21.76 | 29.01 | 43.52 | 58.02 | 65.28 |
| Crospovidone | 2.00 | 2.00 | 2.00 | 2.00 | 2.00 |
| Magnesium stearate | 2.00 | 2.00 | 2.00 | 2.00 | 2.00 |
| Produced | 60 mg | 60 mg | 60 mg | 60 mg | 60 mg |

Examples 20-22

TABLE 6

| Raw and auxiliary materials | Example 2 0.5 mg unit (%) | Example 3 5 mg unit (%) | Example 4 25 mg unit (%) |
|---|---|---|---|
| Compound of formula (I) | 0.83 | 8.33 | 12.50 |
| Butylated hydroxytoluene | 0.63 | 0.63 | 0.115 |
| Microcrystalline cellulose | 31.52 | 29.02 | 27.795 |
| Mannitol | 63.02 | 58.02 | 55.59 |
| Crospovidone | 2.00 | 2.00 | 2.00 |
| Magnesium stearate | 2.00 | 2.00 | 2.00 |
| Produced | 60 mg | 60 mg | 200 mg |

For the formulations described herein, direct tableting was carried out in Examples 15-22 to obtain tablets.

Example 23

A sample prepared according to Example 21 was coated with a film coating premix (Opadry 20A18334-CN, white) purchased from Colorcon and consisted of the following ingredients: HPMC2910 hydroxypropyl methyl cellulose, hydroxypropyl cellulose and titanium dioxide.

Example 24

A compatibility test was carried out with lactose (a reducing sugar) and the compound of formula (I) at room temperature in which, after both were mixed in a certain ratio, the changes of impurity in the compound of formula (I) were tested. The results are shown in the following table:

TABLE 7

| Sample | Main peak area (%) | Number of impurities | Total impurities (%) |
|---|---|---|---|
| Compound of formula (I) | 99.247 | 5 | 0.753 |
| Mixture of the compound of formula (I) and lactose | 98.768 | 13 | 1.232 |

The above data suggest that the impurities increase significantly after the compound of formula (I) and lactose were mixed, indicating a poor compatibility therebetween.

Example 25

A sample prepared according to Example 2 was allowed to stably stand at 60° C. before related substances were tested. It could be seen that the formulated sample was stable. The increase in impurities is shown in the following table:

TABLE 8

| Standing stability at 60° C. | Main peak area (%) | Number of impurities | Maximum single impurity | Total impurities (%) |
|---|---|---|---|---|
| 0 day | 99.648 | 10 | 0.054% | 0.352 |
| 5 days | 99.601 | 11 | 0.055% | 0.399 |
| 10 days | 99.606 | 14 | 0.055% | 0.394 |

Example 26

Samples prepared according to Examples 15-19 were allowed to stably stand at 60° C. before related substances were tested. The results about impurities are shown in the following table:

TABLE 9

| Standing Stability at 60° C. | Main Ingredient (%) | Number of Impurities | Total Impurities (%) | Increase in Total Impurities (%) |
|---|---|---|---|---|
| Example 15 Day 0 sample | 99.630 | 11 | 0.370 | — |
| Example 15 Day 30 sample | 99.073 | 23 | 0.927 | 0.557 |
| Example 16 Day 0 sample | 99.621 | 12 | 0.379 | — |
| Example 16 Day 30 sample | 99.089 | 24 | 0.911 | 0.532 |
| Example 17 Day 0 sample | 99.591 | 14 | 0.409 | — |
| Example 17 Day 30 sample | 99.331 | 18 | 0.669 | 0.260 |
| Example 18 Day 0 sample | 99.625 | 12 | 0.375 | — |
| Example 18 Day 30 sample | 99.392 | 15 | 0.608 | 0.233 |
| Example 19 Day 0 sample | 99.605 | 13 | 0.395 | — |
| Example 19 Day 30 sample | 99.106 | 23 | 0.894 | 0.499 |

The Increase in Total Impurities in the above table refers to the 30-day total impurity data at 60° C. minus the 0-day total impurity data of the corresponding samples. The increase in total impurities at day 30 is correlated to the proportion of materials in the diluent mixed powder in the corresponding formulation. In the case where microcrystalline cellulose and mannitol were used as the diluent mixed powder, the microcrystalline cellulose was preferably comprised in the mixed powder with a percentage of 25%-50% by weight.

Example 27

A sample prepared according to Example 21 was allowed to stably stand before related substances were tested. It could be seen that the formulated sample were stable. The results about impurities are shown in the following table:

TABLE 10

| Standing stability | Main ingredient (%) | Number of impurities | Total impurities (%) |
|---|---|---|---|
| 0 days | 99.109 | 16 | 0.891 |
| 40° C. + 75% 30 days | 98.974 | 16 | 1.026 |
| 60° C. 10 days | 98.947 | 13 | 1.053 |

Example 28

A sample prepared according to Example 22 was allowed to stably stand before related substances were tested. It could be seen that the formulated sample was stable. The results about impurities are shown in the following table:

TABLE 11

| Standing stability | Main ingredient (%) | Number of impurities | Total impurities (%) |
|---|---|---|---|
| 0 days | 99.068 | 16 | 0.932 |
| 40° C. + 75% 30 days | 99.082 | 15 | 0.918 |
| 60° C. 10 days | 98.857 | 18 | 1.143 |

Example 29

A sample prepared according to Example 23 was allowed to stably stand before related substances were tested. It could be seen that the formulated sample was stable. The results about impurities are shown in the following table:

TABLE 12

| Standing stability | Main ingredient (%) | Number of impurities | Maximum unknown single impurity (%) | Total impurities (%) |
|---|---|---|---|---|
| 0 day | 99.026 | 20 | 0.124 | 0.974 |
| 40° C. + 75% 30 days | 98.977 | 16 | 0.125 | 1.023 |
| 60° C. 10 days | 98.857 | 19 | 0.113 | 1.143 |
| 60° C. 23 days | 98.242 | 27 | 0.111 | 1.758 |
| 60° C. 30 days | 98.400 | 25 | 0.130 | 1.600 |

Example 30

A sample was prepared according to the formulation in patent publication WO2015031228A1:

TABLE 13

| Raw materials and auxiliaries | 12.5 mg unit (%) |
|---|---|
| Compound of formula (I) | 15.6 |
| Microcrystalline cellulose | 20.0 |
| Mannitol | 59.9 |
| Crospovidone | 2.0 |
| Magnesium stearate | 2.5 |
| Produced | 80 mg |

For the formulation described here, direct tabletting was carried out to obtain tablets.

A sample prepared according to Example 30 was allowed stably stand at 60° C. before related substances were tested. The results about impurities are shown in the following table:

TABLE 14

| Standing stability at 60° C. | Main ingredient (%) | Number of impurities | Total impurities (%) |
|---|---|---|---|
| Day 0 sample | 99.142 | 15 | 0.858 |
| Day 10 sample | 98.782 | 24 | 1.218 |

From the above results, it could be seen that the sample prepared according to Example 30 had an increase in impurities at 60° C. at day 10 vs. day 0 that was greater than that of the samples in other Examples of the present patent application.

Examples 31-33

TABLE 15

| Raw materials and auxiliaries | Example 31 0.5 mg unit (%) | Example 32 5 mg unit (%) | Example 33 25 mg unit (%) |
|---|---|---|---|
| Compound of formula (II) | 1.00 | 8.33 | 31.25 |
| Microcrystalline cellulose | 60.80 | 60.77 | 46.00 |
| Mannitol | 34.20 | 26.90 | 18.75 |
| Crospovidone | 2.00 | 2.00 | 2.00 |
| Magnesium stearate | 2.00 | 2.00 | 2.00 |
| Produced | 50 mg | 60 mg | 80 mg |

For the formulations described herein, direct tabletting was carried out in Examples 31 and 32 to obtain tablets. For Example 33, a wet granulator was used to produce granules which were then tableted.

Examples 34-36

TABLE 16

| Raw materials and auxiliaries | Example 34 0.5 mg (in free base) unit (%) | Example 35 5 mg (in free base) unit (%) | Example 36 25 mg (in free base) unit (%) |
|---|---|---|---|
| Compound of formula (III) | 1.18 | 9.79 | 36.73 |
| Microcrystalline cellulose | 34.02 | 25.44 | 13.27 |
| Mannitol | 60.8 | 60.77 | 46 |
| Crospovidone | 2 | 2 | 2 |
| Magnesium stearate | 2 | 2 | 2 |
| Produced | 50 mg | 60 mg | 80 mg |

For the formulations described herein, direct tableting was carried out to obtain tablets.

Examples 37-39

TABLE 17

| Raw materials and auxiliaries | Example 37 1 mg (in free base) unit (%) | Example 38 10 mg (in free base) unit (%) | Example 39 30 mg (in free base) unit (%) |
|---|---|---|---|
| Compound of formula (III) | 1.47 | 11.75 | 17.63 |
| Microcrystalline cellulose | 33.731 | 23.478 | 32.372 |
| Mannitol | 60.8 | 60.77 | 46 |
| Crospovidone | 2 | 2 | 2 |
| Magnesium stearate | 2 | 2 | 2 |
| Produced | 80 mg | 100 mg | 200 mg |

For the formulations described herein, direct tableting was carried out to obtain tablets.

Example 40

A formulation comprising the compound of formula (I) was orally administered to monkeys at a dosage of 10 mg/kg, with a duration in which the DPP IV inhibition rate was greater than 80% of 274 hours.

The invention claimed is:

1. A pharmaceutical formulation, comprising auxiliary materials and an active ingredient, the active ingredient being the compound of the general formula (A) and its stereoisomer, or a pharmaceutically acceptable salt or prodrug thereof, wherein the auxiliary materials do not comprise reducing sugars;

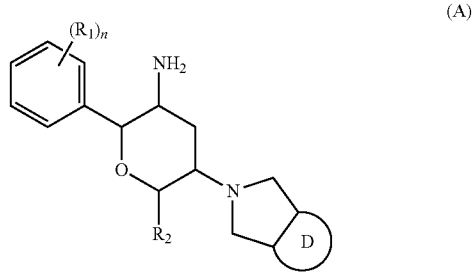

(A)

$R^1$ is each independently selected from H, F, Cl, Br or I;

$R^2$ is each independently selected from H, F, Cl, Br, I or $C_{1-4}$ alkyl, wherein the alkyl is optionally further substituted by 0-4 substituents selected from H, F, Cl, Br or I;

Ring D is selected from a 5-membered heteroaryl ring group, wherein the heteroaryl ring group is optionally further substituted by 0-4 substituents selected from H, $C_{1-4}$ alkyl, $S(=O)_2$—$C_{1-4}$ alkyl or $D^1$, and the heteroaryl ring group contains 2 or 3 N atoms;

$D^1$ is each independently selected from a 5-membered heteroaryl ring group, wherein the heteroaryl ring group is optionally further substituted by 0-4 substituents selected from H or $C_{1-4}$ alkyl, and the heteroaryl ring group contains 2, 3 or 4 N atoms;

n is selected from 0, 1, 2, 3, 4 or 5;

wherein the auxiliary materials comprise a mixture of microcrystalline cellulose and mannitol as a diluent;

wherein the content of the diluent is 40%-96% by weight;

wherein the microcrystalline cellulose in the mixture of microcrystalline cellulose and mannitol has a content selected from 30%-50% by weight;

wherein the auxiliary material further comprises one or more of a lubricant, a glidant, a disintegrant, a surfactant, a wetting agent, and an antioxidant;

wherein, when one or more of the lubricant, the glidant, the disintegrant, the surfactant, the wetting agent, and the antioxidant is present;

the lubricant is selected from one or more of magnesium stearate, calcium stearate, stearic acid, sodium stearyl fumarate, and hydrogenated castor oil;

the glidant is selected from one or more of colloid silica, calcium phosphate, magnesium silicate, and talc;

the disintegrant is selected from one or more of croscarmellose sodium, sodium carboxymethyl starch, crospovidone, and calcium carboxymethyl cellulose;

the surfactant is selected from one or more of glyceryl monooleate, polysorbate, polyvinyl alcohol, and sorbate;

the wetting agent is selected from one or more of poloxamer, polyoxyethylene alkyl ether, polyoxyethylene castor oil derivatives, and polyoxyethylene stearate;

the antioxidant is selected from one or more of vitamin E, alpha-tocopherol, vitamin C and associated sodium or calcium salts thereof, vitamin C palmitate, propyl gallate, octyl gallate, lauryl gallate, butylated hydroxytoluene, and butylated hydroxyanisole;

the lubricant has a content selected from 0.05%-0.1% by weight, 0.05%-0.5% by weight, 0.05%4% by weight, 0.05%-2% by weight, 0.05%-3% by weight, 1%-2% by weight, 1%-3% by weight, 2%-3%, 2%-4% by weight;

the glidant has a content selected from 1%-5% by weight.

2. The pharmaceutical formulation according to claim 1, wherein the pharmaceutical formulation is a solid formulation.

3. The pharmaceutical formulation according to claim 2, wherein the solid formulation is a tablet.

4. A pharmaceutical formulation comprising a unit of 0.10 mg-50 mg of the compound of general formula (A) according to claim 1.

5. A pharmaceutical formulation comprising a unit of 0.1-1 mg, 1-5 mg, 5-10 mg, 10-15 mg, 15-20 mg, 20-25 mg, 25-30 mg, 30-35 mg, 35-40 mg, 40-45 mg or 45-50 mg of the compound of general formula (A) according to claim 1.

6. A pharmaceutical formulation comprising a unit of 0.5 mg, 5 mg, 10 mg, 12.5 mg, 15 mg, 20 mg, 25 mg or 30 mg of the compound of general formula (A) according to claim 1.

7. The pharmaceutical formulation according to claim 1, wherein the pharmaceutical formulation comprises a coating layer.

8. A method for treating diabetes, comprising administration of the pharmaceutical formulation of claim 1 to a subject.

9. The method of the pharmaceutical formulation in the preparation of a medicament for diabetes according to claim 8, wherein the administration is oral administration.

10. The method of the pharmaceutical formulation in the preparation of a medicament for diabetes according to claim 9, wherein the administration includes a regime of: once a day, once a week, once every two weeks or once a month.

11. The method according to claim 8, wherein the compound of general formula (A) is administered in a dosage selected from 1-500 mg/dose.

12. The method according to claim 11, wherein the compound of general formula (A) is administered in a dosage selected from 5 mg/dose, 10 mg/dose, 50 mg/dose, 100 mg/dose, 150 mg/dose, 175 mg/dose, 200 mg/dose, 225 mg/dose, 250 mg/dose.

13. The pharmaceutical formulation according to claim 1, wherein the content of the diluent is 80%-96% by weight.

14. The pharmaceutical formulation according to claim 1, wherein the microcrystalline cellulose in the mixture of microcrystalline cellulose and mannitol has a content selected from 33%-50% by weight.

15. The pharmaceutical formulation according to claim 1, wherein the microcrystalline cellulose in the mixture of microcrystalline cellulose and mannitol has a content selected from 33% by weight.

16. The pharmaceutical formulation according to claim 1, wherein the mannitol in the mixture of microcrystalline cellulose and mannitol has a content selected from 60-70% by weight.

17. The pharmaceutical formulation according to claim 1, wherein $R^1$ is each independently selected from H or F;

$R^2$ is each independently selected from H or trifluoromethyl;

Ring D is selected from imidazole or pyrazole, wherein the imidazole or pyrazole is optionally further substituted by 0-4 substituents selected from H, methyl, ethyl, isopropyl, $S(=O)_2$-methyl, $S(=O)_2$-ethyl, $S(=O)_2$-isopropyl or $D^1$;

$D^1$ is each independently selected from tetrazole, wherein the tetrazole is optionally further substituted by 0-4 substituents selected from H, methyl, ethyl or isopropyl;

n is selected from 0, 1, 2, 3, 4 or 5.

18. The pharmaceutical formulation according to claim 17, wherein the pharmaceutically acceptable salt is selected from benzene sulfonate, salicylate, benzoate, acetate, S-(+)-mandelate, propionate, crotonate, furoate, cinnamate, ethanesulfonate, glycolate, lactate, fumarate, formate, sulfate, hydrobromide, phosphate, trifluoroacetate, tartrate, citrate, glycolate, hydrochloride, p-toluenesulfonate, maleate, succinate, oxalate, methanesulfonate, malonate or malate.

19. The pharmaceutical formulation according to claim 18, wherein the compound of formula (A) is selected from one of the following structures:

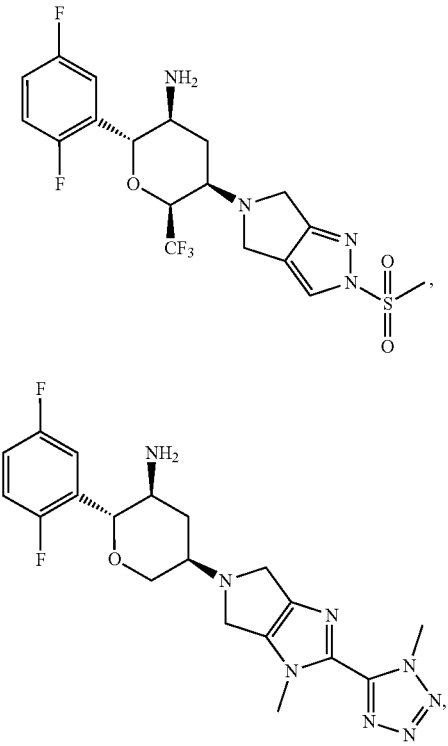

(I)

(II)

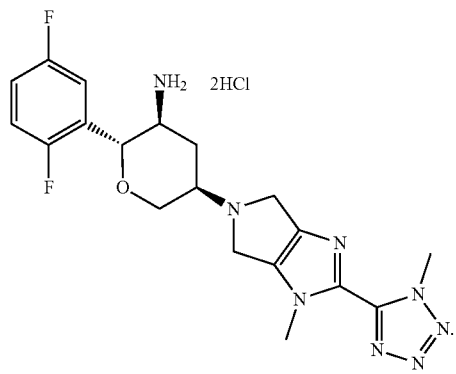

(III)

20. The pharmaceutical formulation as claimed in claim 1, wherein the lubricant has a content selected from 1%-3% by weight.

21. The pharmaceutical formulation as claimed in claim 1, wherein the lubricant has a content selected from 2%-3% by weight.

22. The pharmaceutical formulation according to claim 7, wherein the coating layer is prepared with a coating powder without plasticizer.

* * * * *

UNITED STATES PATENT AND TRADEMARK OFFICE
CERTIFICATE OF CORRECTION

PATENT NO. : 11,974,985 B2
APPLICATION NO. : 16/967534
DATED : May 7, 2024
INVENTOR(S) : Yi Mo et al.

It is certified that error appears in the above-identified patent and that said Letters Patent is hereby corrected as shown below:

In the Specification

Column 8, Line 32 reads: "...pharmaceutical formulation is selected from 0.05%41% by..." but it should read: "...pharmaceutical formulation is selected from 0.05-1% by..."

Column 9, Line 14 reads: "...0.1%-50% by weight, 0.1%4% by weight, 0.1%-2% by..." but it should read: "...0.1%-50% by weight, 0.1%-1% by weight, 0.1%-2% by..."

Signed and Sealed this
Twenty-fifth Day of June, 2024

Katherine Kelly Vidal
*Director of the United States Patent and Trademark Office*